United States Patent [19]

Brück et al.

[11] 4,150,243

[45] Apr. 17, 1979

[54] PROCESS FOR THE DEALKYLATION OF TERT.-ALKYL SUBSTITUTED PHENOLS

[75] Inventors: Dieter W. Brück, Cologne; Helmut Fiege, Leverkusen; Johann Renner, Leverkusen; Feliks Bitners, Leverkusen; Josef Haydn, Leverkusen; Karlfried Wedemeyer, Cologne, all of Fed. Rep. of Germany

[73] Assignee: Bayer Aktiengesellschaft, Leverkusen, Fed. Rep. of Germany

[21] Appl. No.: 744,211

[22] Filed: Nov. 22, 1976

[30] Foreign Application Priority Data

Dec. 5, 1975 [DE] Fed. Rep. of Germany ....... 2554702

[51] Int. Cl.² ............................................. C07C 39/04
[52] U.S. Cl. .................................................. 568/805
[58] Field of Search ............... 260/621 D, 624, 624 E; 568/805

[56] References Cited

U.S. PATENT DOCUMENTS

| | | | |
|---|---|---|---|
| 2,290,603 | 7/1942 | Stevens et al. | 260/621 D |
| 2,297,588 | 9/1942 | Stevens | 260/621 D |
| 2,366,497 | 1/1945 | Dawson | 260/682 |
| 2,497,971 | 2/1950 | Basterfield | 260/624 A |
| 3,465,048 | 9/1969 | Ito et al. | 260/621 D |
| 3,714,269 | 1/1973 | Ito et al. | 260/621 R |

Primary Examiner—Werren B. Lone
Attorney, Agent, or Firm—Sprung, Felfe, Horn, Lynch & Kramer

[57] ABSTRACT

A process for the tertiary dealkylation of a tertiary alkyl containing m- and/or p-cresol wherein a tertiary alkyl containing m- and/or p-cresol is continously introduced into a reaction vessel with a small amount of sulfuric acid or an quivalent amount of a sulfonic acid and the reaction vessel contains a high concentration of m- and/or p-cresol or a high boiling phenol which under the prevailing reaction conditions is not substantially vaporized from the reaction mixture. The reaction mixture is maintained at a temperature of no greater than 230° C. The reaction products are withdrawn continuously from the reactor (and separated into its components) and at the same time a small amount of the reaction mixture being withdrawn intermittently or continously from the reactor.

20 Claims, 2 Drawing Figures

PROCESS FOR THE DEALKYLATION OF TERT.-ALKYL SUBSTITUTED PHENOLS

The invention relates to a process for the preparation of m-cresol and p-cresol by continuous dealkylation of the corresponding mono- and/or di-tert.-alkyl-cresols.

Because the difference between the boiling points of m-cresol and p-cresol is small it is virtually impossible to separate mixtures of these compounds by distillation. Amongst the separation processes proposed hitherto, the so-called butylation of the mixtures, separation of the resulting mono- and/or di-tert.-butyl-cresols by distillation and subsequent debutylation to give the pure cresols has achieved great importance (Ind. Eng. Chem. 35 (1943), pages 655 to 660). Since m-cresol and p-cresol are very important as organic intermediate products, a debutylation process which operates continuously, with a high yield and with a low production of by-products and which is reliable in operation is of great importance for the large scale industrial separation of cresols.

The dealkylation of tert.-alkyl-substituted phenols can be carried out by the action of heat or in the presence of a catalyst. Preferably, the dealkylation is carried out in the liquid phase in the presence of an acid catalyst, preferably sulfuric acid (compare DT-AS (German Published Specification) No. 1,230,432, column 1, lines 9 to 38).

Although sulphuric acid, as the catalyst for the dealkylation in the liquid phase, is particularly readily accessible, highly active and completely soluble in the reaction mixture, its use in the concentration of 0.1 to 1 percent by weight of the starting material, which was customary hitherto, does however have various disadvantages, in particular its corrosive action and the fact that it promotes undesirable redox side reactions and polymerisation of the isobutene which is eliminated (U.S. Pat. No. 2,297,588, page 2, right-hand column, lines 47 to 65).

A continuous process for the dealkylation of mono- and/or di-tert.-alkyl-substituted cresols which can be carried out on an industrial scale has hitherto been unknown. However, such a process is the prerequisite for a feasible continuous preparation of m-cresol and p-cresol.

SUMMARY OF INVENTION

Broadly, this invention contemplates a process for the tertiary dealkylation of a tertiary alkyl containing m- and/or p-cresol which comprises continously introducing a tertiary alkyl m- and/or p-cresol and sulfuric acid in an amount of less than 0.1% by weight sulfuric acid based upon the weight of the introduced mixture or an equivalent amount of a sulfonic acid into a reaction vessel containing m- and/or p-cresol and/or optionally a higher boiling phenol which under the prevailing reaction conditions is not substantially vaporized from the reaction mixture, withdrawing continously the reaction products from the reaction vessel, maintaining said reaction mixture at a temperature of no greater than 230° C., said reaction mixture comprising a major amount of said m- and/or p-cresol and/or optionally of said higher boiling phenol together with the not yet reacted part of the introduced mixture, and intermittently or continously withdrawing a potion of said reaction mixture.

It has now been found that m-cresol and/or p-cresol can be prepared particularly advantageously from mono- and/or di-tert.-alkyl-m and/or -p-cresol by means of dealkylation, wherein the dealkylation is carried out at a temperature no greater than 230° C. and the feed product to be dealkylated, together with less than 0.1% by weight of sulphuric acid, or the equivalent amount of a sulphonic acid, based on the weight of the feed product, are fed continuously into a reactor vessel, a high cresol concentration being maintained in the reaction mixture, and wherein the reaction products are withdrawn continuously from the reactor vessel, while small amounts of the reaction mixture are withdrawn intermittently or continuously from the reactor vessel.

Here and in the text which follows, dealkylation and debutylation are to be understood as the elimination of lower tertiary alkyl groups, in particular of tert.-butyl groups, but not as the elimination of other alkyl groups and butyl groups which are not bonded to the aromatic ring by means of a tertiary carbon atom.

The process according to the invention can be employed particularly advantageously for the debutylation of butylated m-cresol or p-cresol, which can be obtained by butylation of mixtures of m-cresol and p-cresol and subsequent separation of the butylated products by distillation, so that pure m-cresol or p-cresol is obtained.

However, it is also possible advantageously to debutylate mixtures of butylated m- and p-cresol in the same way; the choice of the starting material depends on economical considerations rather than on technical considerations. When selecting the starting material, the desired purity will be a factor equally as decisive as the availability of the material. Of course, the starting material can also contain cresol which is not butylated.

m-Cresol and p-cresol and the butylation thereof to give the corresponding mono- and di-tert.-butyl-cresols are known. Materials which can be debutylated are, in particular: 4-methyl-2-tert.-butyl-phenol, 4-methyl-2,6-di-tert.-butyl-phenol, 3-methyl-4-tert.-butyl-phenol, 3-methyl-6-tert.-butyl-phenol and 3-methyl-4,6-di-tert.-butyl-phenol.

The reaction temperature in the process according to the invention can be up to 230° C. The reaction is preferably carried out at an internal temperature, in the reactor, of 180° to 220° C. and especially of between 190° and 210° C.

Customary apparatuses according to the state of the art that is to say heat exchangers which have a heating surface which is adequate for transfer of the heat of fission and the heat of vaporisation, are suitable for carrying out the process according to the invention. For example, vaporisers which operate with natural circulation or with forced circulation of the liquid and contain heating tubes or heating plates arranged vertically, obliquely and/or horizontally in internal and/or external heating chambers may be mentioned. A stirred kettle in which the heating surface has optionally been enlarged by internal or external heat exchange surfaces can also be suitable.

The reaction volume of the reactor vessel is appropriately of the order of size of the volume of the liquid feed material put through per hour.

The reactor vessel can be operated under normal pressure, under slightly reduced pressure or under a slight excess pressure. Preferably, the reaction is carried out in the pressure range between 0.5 and 1.5 bars.

In the process according to the invention, sulphuric acid is preferably used as the catalyst; the amount of this acid is less than 0.1% by weight, based on the weight of the feed product. The amount of sulphuric acid employed can be almost up to 0.1% by weight, based on the total weight of the feed product, but 0.005 to 0.5% by weight of $H_2SO_4$ are preferably used.

In general, the sulphuric acid used is concentrated sulphuric acid, that is to say sulphuric acid which contains 96 to 98 percent by weight of $H_2SO_4$ (remainder $H_2O$). Of course, it is also possible to use more highly concentrated sulphuric acid, for example oleum with any desired contents of $SO_3$, or $SO_3$ itself, in an equivalent amount.

It is known that cresols and alkylphenols readily form the corresponding sulphonic acids with concentrated sulphuric acid. In the process according to the invention, the corresponding sulphonic acids can also be used, in an equivalent amount, as catalysts. Generally, sulfonic acid is employed in an amount of 0.005 to 1.0% by weight, based upon the weight of the introduced mixture. It is also possible to employ other sulphonic acids in an equivalent amount and acids which can be used for this purpose are aromatic sulphonic acids, but also aliphatic, cycloaliphatic and araliphatic sulphonic acids. Sulphuric acid can be introduced into the reactor vessel continously or intermittently, direct or after prior mixing with the feed product or with part of the feed product. It is advantageous continously to meter in concentrated sulphuric acid in the appropriate amount. In order to achieve better metering, it can also be advantageous to dissolve sulphuric acid, or the equivalent amount of a sulphonic acid, in the reaction mixture or in cresol, or to mix the acid with these compounds, and to introduce this solution or mixture into the reactor vessel, as indicated above.

An essential characteristic of the process according to the invention is a high concentration of cresol in the reaction mixture. This can amount to, for example, 50 to 90 percent by weight of the reaction mixture; preferably, a concentration of 60 to 70 percent by weight is maintained.

The high concentration of cresol in the reaction mixture is generally maintained by recycling into the reactor vessel part of the cresol which issues from the reactor vessel as the reaction product.

Of course, it is also possible to add an appropriate amount of cresol to the feed material from the start. Advantageously, the cresol which is formed during the dealkylation will be chosen for this purpose, since no additional separation problems then arise. However, it is also possible to use a corresponding high-boiling phenol, e.g. with a boiling point of from 180° to 250° C., which, at the reaction temperature, does not leave the reactor vessel with the gaseous reaction products, or which does so to only a very small extent, and which can be separated easily from these reaction products. It is optionally also possible to use another diluent which is inert under the reaction conditions, in place of cresol.

The continous withdrawal of a small amount of the liquid reation mixture is highly essential for continous operation of the dealkylation. Without this withdrawal, for example, the reaction ceases after a troughput which corresponds to approximately 40 times the reaction volume. An increase in the amount of catalyst can indeed lead to the reaction being initiated again for a short time but this increases the danger that the enrichment of sulphuric acid, and of its secondary products, in the reaction mixture will lead to very sudden, highly exothermic, and thus dangerous, decompositions.

The withdrawal, according to the invention, of a small part of the liquid reaction mixture can be effected continuously or intermittently. In general, it is appropriate to withdraw from the system up to 10, preferably 2 to 6, percent by weight of the reaction mixture, based on the amount of feed product introduced.

In general, it is advantageous to keep the mass of the reaction mixture constant. This can be effected in various ways. Advantageously, the reaction can be carried out with a constant supply of the feed product and at constant temperature of the reaction mixture and the withdrawal of part of the reaction mixture can be regulated, for example by means of a sump level indicator. When the activity, in respect of scission, of the reaction mixture subsides, and the mass thus increases, the amount withdrawn is increased until the original activity, in respect of scission, is achieved by feeding in fresh feed material. Conversely, when the activity, in respect of scission, increases, the amount withdrawn is reduced, so that the mass of the reaction mixture remains constant.

It is also possible to keep constant the amount withdrawn and, at a constant temperature, to keep the mass of the reaction mixture constant by appropriate control of the supply of the feed material and of the catalyst.

Furthermore, it is possible, when the supply of material and of catalyst is constant and the withdrawal of part of the reaction mixture is also constant, to regulate the temperature and thus to control, by means of the activity, in respect of scission, or rate of reaction, which corresponds to the temperature, the amount of the gas mixture which flows out of the reactor and the mass of the reaction mixture present in the reactor.

In a further embodiment it is also possible, for a constant supply of feed material and of catalyst, to control the mass of the reaction mixture in accordance with the temperature by indicating a set temperature and controlling the partial amount of the reaction mixture which is to be withdrawn from the reactor by means of the difference between the actual temperature and the set temperature, so that when the actual temperature exceeds or falls below the set temperature a larger or smaller partial amount is withdrawn.

The reaction mixture which is withdrawn can, for example, be purified by distillation to remove undesirable by-products, such as resins, and can then be recycled, optionally as a mixture with fresh feed product, into the reactor. For example, it can be distilled under reduced pressure and the distillate which passes over can be re-used as reaction material; for example, in the case of the debutylation of di-tert.-butylcresol, about 95–98% by weight of the material withdrawn passes over as the distillate under a pressure of 22 mm Hg and at a vapour temperature of about 150° C. The feed material actually lost, which is obtained in the form of a resinous residue from this distillation, amounts in general to less than 0.2% by weight, based on the butylcresol employed.

As mentioned, a high concentration of cresol in the reaction mixture can advantageously be maintained by recycling into the reaction mixture, part of the cresol which leaves the reactor as the reaction product.

In the text which follows the dealkylation according to the invention is described in more detail, using debutylation as an example.

Recycling of the cresol can be effected, for example, by subjecting the gas mixture which issues from the reactor vessel and which contains isobutene, low-boiling impurities, cresol and mono-tert.-butyl-cresol, direct to fractionation. The gas mixture is fed into a fractionation unit, for example a distillation column, in which the mono-tert.-butyl-cresol is optionally completely separated off and partial separation of the cresol from isobutene and the low-boiling impurities is effected. The liquid, that is to say cresol and mono-tert.-butyl-cresol, which flows off from the fractionation unit is recycled into the reactor vessel.

The gas which issues from the fractionation unit and which, in addition to isobutene, contains low-boiling impurities and the remainder of the cresol, as well as, in some cases, also mono-tert.-butyl-cresol, is then fed into a temperature-controlled condenser, for example a dephlegmator, in which partial condensation of the gas is effected, the condensate containing mainly cresol. This condensate is recycled as reflux to the fractionation unit.

The concentration of cresol in the reactor vessel can thus be controlled by the temperature set for the condenser, that is to say by means of its reflux ratio. In this context the reflux ratio is defined not in accordance with the definition otherwise given but as the ratio of the amount of residual gas which issues from the condenser to the condensate which flows off.

In the fractionation stage, the fractionation of the gases which issue from the reactor vessel can be carried out in the temperature range between 100° and 220° C. under 600 to 1,000 mm Hg and using a reflux ratio of 1 to 3. It can be particularly advantageous to carry out the fractionation in the temperature range from 150° to 210° C. under 700 to 900 mm Hg and using a reflux ratio of 1.5 to 2. The residual gas which has not been condensed and which contains isobutene, low-boiling impurities, cresol and, in some cases, mono-tert.-butyl-cresol, can be worked up in a known manner in a further fractionation stage; for example, cresol can be separated off and the higher-boiling constituents, such as cresol, can be recycled into the reactor vessel.

In the text which follows, a fractionation stage is to be designated as an apparatus, for example a distillation column, which, by means of an appropriate number of separation steps (for example height of the distillation column) and the reflux ratio chosen, gives the desired separation result.

According to a particular variant of the process according to the invention the gas mixture which issues from the fractionation unit or fractionation stage, as described above, is subjected to partial condensation, for example in a dephlegmator, only after it has flowed through a second fractionation stage. The liquid which flows off from the second fractionation stage and which is virtually pure cresol is recycled to the first fractionation stage only in part, corresponding to a reflux ratio of 1 to 2 and preferably 1.2 to 1.5. The remaining residue is withdrawn as product. With this procedure it is advantageous to work at a dephlegmator temperature of 20° to 30° C., preferably 25° C., measured in the uncondensed gas, and with a reflux ratio of 30 to 80, preferably 50 to 60.

BRIEF DESCRIPTION OF DRAWINGS

Referring to the drawings herein.

DESCRIPTION OF SPECIFIC EMBODIMENTS

One possibility for carrying out the process according to the invention industrially is shown diagrammatically in FIG. 1 and will be described below.

Mono- and/or di-butylcresol is metered, via line 1, together with sulphuric acid, via line 2, and, optionally, the distillate from the sump product which is withdrawn from reactor vessel 22 via line 3 and worked up and which contains cresol and mono- and/or di-butylcresol, via line 5, into the reactor vessel 22. The gas mixture 6 (isobutene, cresol and monobutylcresol) formed during the reaction is fed (streams 6 and 8) through the two fractionation stages 23 and 24, which are connected in series, and finally (streams 13 and 18) is subjected to partial condensation in the dephlegmators 27 and 28, for example at 25° C. and 0° C. Whilst all of the condensate 7 (cresol and monobutylcresol) which flows out of the first fractionation stage 23 flows back to reactor vessel 22, the condensate 9 (cresol with, for example, about 0.1 to about 0.3% of low-boiling compounds and 0.1 percent by weight of monobutylcresol) which flows from the second fractionation stage 24 is recycled only in part (for example 2 parts reflux, 1 part take-off) to the first fractionation stage 23. The reaction product, that is to say cresol, can be withdrawn in the virtually pure form from this stream 9 of condensate via 16. The low-boiling by-products (low-boiling compounds) which are also formed in small amounts during the debutylation, are withdrawn from the streams 15 of condensate, via a very small condensate take-off 17, for example at a reflux ratio which is equal to, or greater than, 50, and together with the stream 19 of condensate recovered and/or recycled to alkylation.

The isobutene 20 which issues from the second dephlegmator 28 can be recycled into the alkylation of the mixture of cresols. For start-up, the reactor vessel 22 can be filled with pure cresol and heated to the reflux temperature of cresol (for example 202° C. under 760 mm Hg).

The part of the reaction mixture which is continuously or intermittently withdrawn from reactor vessel 22 via 3 can also be purified, continuously or intermittently, in the distillation 21 in order to remove high-boiling, resin-like by-products, which are taken off via 4, and, after condensation has taken place, can optionally be recycled, via a collection vessel, through 5 into the reactor. In general, this purification can also be carried out in a separate apparatus, independently of the process described above; advantageously, it can then be incorporated in the continuous operation of the process according to the invention when the throughput per hour is correspondingly high, so that continuous operation of this measure, which in itself is not essential to the process according to the invention, is reasonable.

A further possibility for carrying out the process according to the invention industrially is shown diagrammatically in FIG. 2 and will be described below.

Reactor vessel 22 is charged through lines 1,2 and, optionally, 5, as described above. Part of the reaction mixture is taken off via 3 and optionally purified in the distillation 21, as described above. The gas mixture 6 which issues from the reactor vessel passes into the first fractionation stage 23, from which the condensate 7 is recycled into the reactor vessel 22. The gas mixture 8 which issues from the first fractionation stage 23 is fed into a temperature-controlled dephlegmator 25, which so maintains a reflux ratio (ratio of the gas mixture 10, which issues and flows to the dephlegmator 26, to the condensate 9, which flows off), which is defined in a manner which differs from the customary definition, of, for example, 1.5 to 2 that the condensate which flows out of the second dephlegmator 26 to the second fractionation stage 24 contains less than 1% by weight of monobutylcresol. The residual gas flows via 12 to the final dephlegmator 28.

The low-boiling compounds and monobutylcresol still contained in the condensate 11 are separated off in the second fractionation stage 24. Monobutylcresol, which, for example, has been enriched to a cresol content of about 30% by weight, flows from this second fractionation stage 24 via line 14 back into reactor vessel 22, whilst the residual gas passes via 13 into the dephlegmator 27. Virtually pure cresol is taken off from fractionation stage 24 via a side stream take-off 16. The streams of residual gas 12 and 18 which issue from the dephlegmators 26 and 27 and have a temperature of, for example, about 25° C., pass into a final dephlegmator 28, from which virtually only isobutene issues as gas via 20. The low-boiling by-products (low-boiling compounds) are withdrawn from the system, both from the stream 15 of condensate, via a small condensate take-off 17, for example at a reflux ratio which is equal to, or greater than, 100, and via the stream 19 of condensate.

The optionally continuous purification of the part of the reaction mixture which is withdrawn from reactor vessel 22 can be carried out as described above.

It is surprising that the process according to the invention can be carried out. As can be seen from U.S. Pat. No. 2,290,602, it had to be expected that immediate removal of the debutylated cresol from the reaction mixture would be advantageous since, as a result, dilution of the reaction mixture and a lowering of the catalyst:butylcresols ratio would be avoided (page 3, left-hand column, lines 3 to 19).

The advantages of the process according to the invention on the one hand already lie in the industrially and economically advantageous continuous operation and, on the other hand, lie in the fact that m- and p-cresols can be obtained in high purity (>99.5%) and in a very good yield (equal to, or greater than, 95%) and, moreover, isobutene can also be recovered in high purity (>99.8%).

Furthermore, sulphuric acid, which is readily accessible, is used as the catalyst in a concentration which is lower than that in the state of the art and, as a result, the formation of high-boiling by-products (resins) and the corrosion of the reactor vessel are correspondingly reduced. As a result of the withdrawal, according to the invention, from the system of part of the reaction mixture, the mass of the reaction mixture advantageously being kept constant, the reaction is prevented from going out of control, as a result of undesirable exothermic side reactions and a lowering of the reactivity and of the rate of reaction are also prevented and, thus, a throughput which is constant in time is achieved. By means of the measures of the process according to the invention it is possible for the first time to carry out continuous debutylation over any desired periods of time.

Where parts are indicated in the examples which follow these are parts by weight.

EXAMPLE 1

Figure 1:
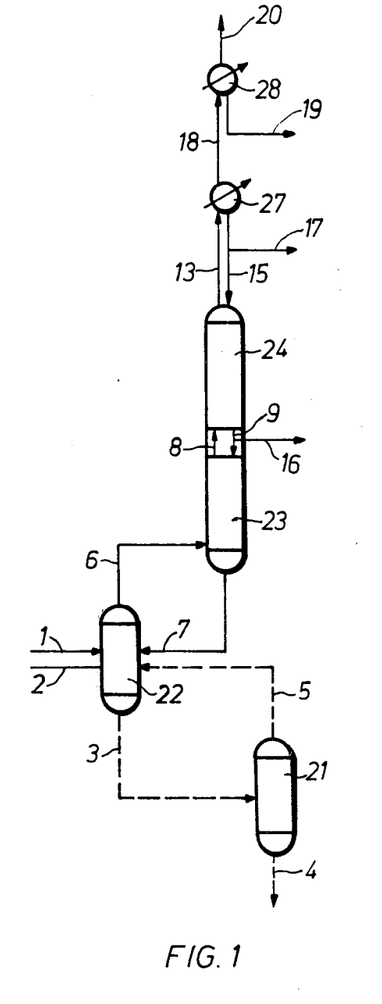
FIG. 1 is a flow diagram showing one method by which the process of the invention can be performed.

The apparatus used corresponded to the process variant shown diagrammatically in FIG. 1.

Before the start of the reaction, the reactor vessel 22, which consists of a circulatory vaporiser which has a reaction volume which approximately corresponds to the throughput per hour, is filled with m-cresol and warmed to the reflux temperature of cresol. Subsequently, 650 parts of 3-methyl-2,6-di-tert.-butyl-phenol are supplied per hour via line 1 and 0.5 part of concentrated sulphuric acid is supplied per hour via line 2.

The reaction temperature is 210° C. and the internal pressure in reactor 22 is about 800 mm Hg.

The gas mixture which issues from reactor vessel 22 flows through 2 fractionation stages 23 and 24, which are connected in series, and passes into the water-cooled dephlegmator 27 and then into the downstream brine-cooled dephlegmator 28.

The isobutene which has not condensed passes from there via line 20 into cold traps, in which it is condensed.

Whilst virtually all (reflux ratio about 50) of the condensate which flows from the water-cooled dephlegmator 27 flows back again, via 15, to the second fractionation stage 24, only a certain portion of the condensate which flows from the second fractionation stage via line 9 is recycled, at a reflux ratio of about 1.2 to 1.5, to the first frctionation stage, whilst the remaining part of this condensate is taken off as product (m-cresol) via line 16.

The removal of part of the reaction mixture from the system is effected via the take-off line 3 and is automatically so controlled that the mass of the reaction mixture remains constant.

On average, about 12.3 parts of the reaction mixture, which has the following composition: 62% of m-cresol, 30% of mono-tert.-butyl-m-cresol, 2% of di-tert.-butyl-m-cresol and 6% of high-boiling by-products, are withdrawn from the system per hour.

About 324.2 parts of isobutene, which has a purity of more 99.9%, flowed per hour from the dephlegmator 28 via 20.

Per hour, about 7.6 parts of a mixture which consists mainly of low-boiling compounds and has the following composition: 13.5% of isobutene, 50.0% of other low-boiling impurities and 36.5% of m-cresol, leave the brine-cooled dephlegmator 28 at 0° C. via 19, as the condensate.

About 1 part of a condensate which has the following composition: 5% of low-boiling impurities and 95% of m-cresol, is taken off per hour via 17 from the stream 15 of condensate which recycles at about 25° C. from the water-cooled dephlegmator 27.

When the temperature at the top of fractionation stage 24 (temperature of the stream 13 of gas which issues from 24) is about 90° C., the pressure at the top is 760 mm Hg and the temperature of the reflux 9 which flows to the first fractionation stage 23 is about 156° C. and the reflux ratio R/T is 1.5, 304.9 parts of m-cresol in a purity of 99.5% (0.3% of low-boiling impurities and 0.2% of mono-tert.-butyl-m-cresol) are obtained per hour via the product take-off 16.

The yield corresponds to 97% of theory, based on the feed material; it must be taken into account that part of the feed material is continuously withdrawn from the system and the yield is therefore even higher when based on converted feed material.

EXAMPLE 2

Figure 2:
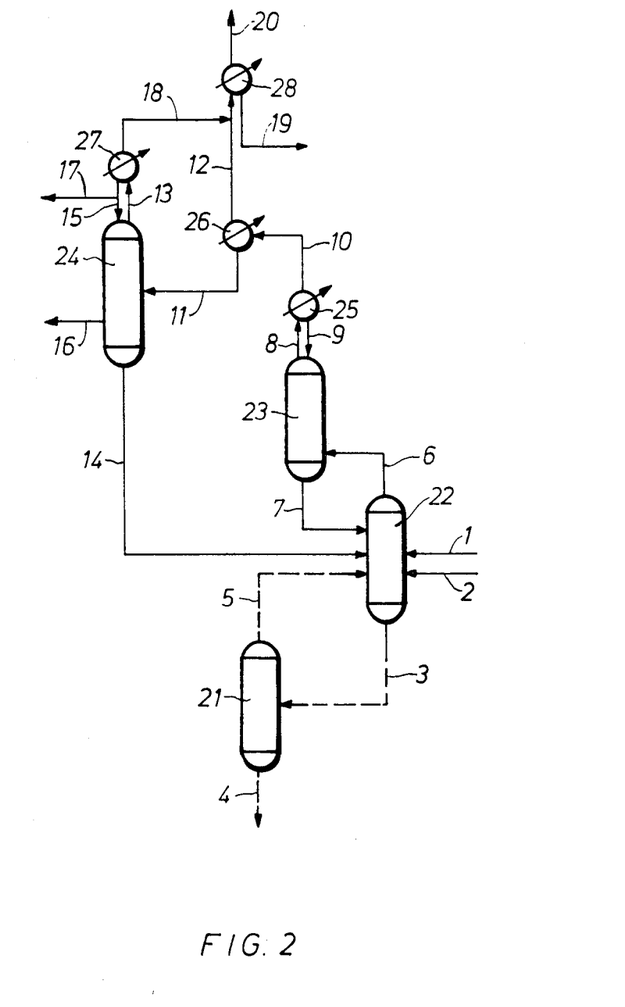
FIG. 2 is another flow diagram, similar to FIG. 1 in respect of reference numerals and parts, showing another method by which the process of the invention can be performed.

A laboratory apparatus corresponding to the above process variant, which is shown diagrammatically in FIG. 2, is used in this example.

Reactor vessel 22 again consists of a circulatory vaporiser which has a reaction volume which corresponds approximately to the throughput per hour.

Reactor vessel 22 is filled with m-cresol and warmed to the reflux temperature of m-cresol.

Subsequently, 650 parts of 3-methyl-2,6-di-tert.-butylphenol are supplied per hour via line 1 and 0.2 part of concentrated sulphuric acid (98% by weight of $H_2SO_4$, remainder water) is supplied per hour via line 2.

On average, about 24.7 parts of the reaction mixture, which has the following composition: 65% of m-cresol, 30% of mono-tert.-butyl-m-cresol, 1% of di-tert.-butyl-m-cresol and 4% of high-boiling by-products, are withdrawn from the system per hour via line 3 by means of automatic control of the contents of the reactor on the basis of the mass of the reaction mixture.

The temperature in reactor vessel 22 is about 210° C. and the pressure, measured in the brine-cooled condenser 28, is about 760 mm Hg.

The gas mixture which issues from reactor vessel 22 flows through the first fractionation stage 23 and is partially condensed in a temperature-controlled dephlegmator 25; the control is carried out in such a way that the vapours which flow out into a second water-cooled dephlegmator 26 are at a temperature of about 165° C. and a ratio of the amount of condensate to the amount of gas which has not condensed (reflux ratio) of 1.5–2 is maintained at the top of the first fractionation stage 23.

The condensate 11, which issues from dephlegmator 26 and flows, at a temperature of about 150° C., to the second fractionation stage 24, contains about 4% of low-boiling impurities, 95.5% of m-cresol and about 0.5% of mono-tert.-butyl-m-cresol.

This condensate is worked up in the second fractionation stage 24 at a sump temperature of about 215° C. and at a reflux ratio of about 100. Whilst the sump product 14, which flows from the second fractionation stage 24 and contains about 76% of m-cresol and 24% of mono-tert.-butyl-m-cresol, is recycled to reactor vessel 22, the m-cresol which is free from low-boiling compounds is taken off in sidestream 16 and the gas mixture 13, which issues at the top of fractionation stage 24, is partially condensed at about 25° C. in a further water-cooled dephlegmator 27.

The streams 12 and 18 of residual gas which issue from the dephlegmators 26 and 27 pass into a brine-cooled dephlegmator 28, from which the condensate, which is at about 0° C., is removed via 19.

The isobutene which has not condensed in dephlegmator 28 is taken off via 20 and condensed. 321.8 Parts of isobutene (purity more than 99.9%) are obtained per hour.

290.6 Parts of m-cresol in a purity of 99.8% (remainder mono-tert.-butyl-m-cresol) are obtained per hour via the product take-off 16.

The low-boiling impurities are removed from the system via the take-offs 19 and 17, 4.6 parts of a mixture of 63.5% of isobutene and other low-boiling compounds and 36.5% of m-cresol being obtained per hour as the condensate in dephlegmator 28 and 8.5 parts of a mixture of 22.7% of isobutene and other low-boiling compounds and 77.3% of m-cresol being taken off, as a sidestream, from the condensate reflux of dephlegmator 27.

EXAMPLE 3

The part of the reaction mixture withdrawn from the system in Examples 1 and 2 is distilled in a fractionation unit under a top pressure of about 22 mm Hg up to a vapour temperature of about 155° C., 96.5% of the material employed being obtained as the distillate.

In the apparatus described in Example 2, reactor vessel 22 is filled with m-cresol and warmed to the reflux temperature of m-cresol. Subsequently, 650 parts by weight of 3-methyl-2,6-di-tert.-butylphenol are supplied per hour via line 1 and 35.9 parts of the distillate obtained as described above are supplied per hour via line 5 and 0.1 part of concentrated sulphuric acid is supplied per hour via line 2.

In other respects the procedure is as described in Example 2. The following products are obtained: 312 parts of m-cresol (purity 99.8%, remainder mono-tert.-butyl-m-cresol) and 322.4 parts of isobutene (purity more than 99.9%).

37.2 Parts of a mixture having the following composition: 70% of m-cresol, 28% of mono-tert.-butyl-m-cresol, 1% of di-tert.-butyl-m-cresol and 1% of high-boiling impurities, are withdrawn from the system.

The low-boiling impurities withdrawn from the system via take-off 17 are 4.8 parts of a mixture of 22.7% of isobutene and low-boiling impurities and 77.3% of m-cresol and those withdrawn from the system as condensate 19 are 9.5 parts of a mixture of 63.5% of isobutene and low-boiling impurities and 36.5% of m-cresol.

EXAMPLE 4 (Comparison Example)

The laboratory apparatus described in Example 2 is used.

Reactor vessel 22 is filled with m-cresol and warmed to the reflux temperature of m-cresol. Subsequently, 650 parts of 3-methyl-2,6-di-tert.-butylphenol are supplied per hour via line 1 and 0.1 part of concentrated sulphuric acid is supplied per hour via line 2. On the other hand, there is no withdrawal of reaction mixture from the system via line 3 as described in Example 2.

The reaction temperature at the start of the reaction was 210° C. and the pressure, measured in the brine-cooled condenser 28, is 760 mm Hg. After about 20 hours the rate of reaction progressively slows down and, at the same time, the temperature of the reaction mixture rises by about 20 to 30° C. above the temperature of the heating medium.

By means of a stepwise increase in the amount of sulphuric acid added per hour, up to, finally, 1.5 parts, it is possible to start the reaction again each time; however, it always virtually ceases again after about 10 to 20 minutes.

Finally, the temperature of the reaction mixture rises suddenly as a result of the exothermic side reactions, so that an internal temperature of more than 300° C. is reached.

The experiment is then discontinued.

EXAMPLE 5

The apparatus described in Example 1 is used.

Before the start of the reaction, reactor vessel 22 is filled with p-cresol and warmed to the reflux temperature of p-cresol. Subsequently, 650 parts by weight of 4-methyl-2,6-di-tert.-butylphenol are supplied per hour via line 1 and 0.2 part of concentrated sulphuric acid is supplied per hour via line 2.

On average, 22.2 parts of the reactor mixture, which has the following composition: 65% of p-cresol, 29% of mono-tert.-butyl-p-cresol, 1.5% of di-tert.-butyl-p-cresol and 4.5% of high-boiling by-products, are withdrawn from the system per hour, via line 3, by means of the automatic control described.

The temperature of the reaction mixture is about 210° C. and the internal pressure in the reactor is about 800 mm Hg.

In other respects the procedure is as described in Example 1.

297.4 Parts of p-cresol in a purity of 99.5% (0.3% of low-boiling by-products and 0.2% of mono-tert.-butyl-p-cresol) are obtained via line 16; 321.4 parts of isobutene in a purity of more than 99.9% are obtained via line 20; 7.8 parts of a mixture of 61% of isobutene and low-boiling impurities and 39% of p-cresol are obtained as the condensate from dephlegmator 28 and 1.2 parts of a mixture of 5% of low-boiling impurities and 95% of p-cresol are removed from the system via the side take-off 17.

EXAMPLE 6

The apparatus consists of a stirred kettle which had a reaction volume of about 300 ml and which can be heated by means of thermostat-controlled jacket heating. The vapours leaving the stirred kettle pass into a silver-jacketed column 60 cm in length and 2.5 cm in diameter, which is filled with VA steel wire mesh rings. The vapours passed from the volumn into a column head and the condensate from this head is fed, at a reflux ratio of 2, to the column, from which it flows back further into the stirred kettle. The remaining part of the condensate is collected in a collection vessel.

The vapours leaving the column head flow through a water-cooled intensive cooler and the condensate flowing from this is also collected in the collection vessel, whilst the gases which do not condense, that is to say isobutene, are condensed at −78° C. in two downstream cold traps.

Part of the reaction mixture is automatically withdrawn via an overflow which limits the reaction volume in the stirred kettle and the supply of reaction mixture to the stirred kettle is designed in such a way that only a small amount of the reaction mixture flows off when the reaction is in the desired steady state.

At the start of the reaction the stirred kettle is filled with mono-tert.-butyl-m-cresol and this is heated to the boil.

235 Parts of mono-tert.-butyl-m-cresol and 0.075 part of 98% strength by weight sulphuric acid are then added per hour.

During the reaction, the temperature in the reaction space is about 200° C. and the internal pressure is about 780 mm Hg, whilst the pressure in the column head is about 760 mm Hg. Per hour, about 78 parts of isobutene in a purity of more than 99.9% are obtained, whilst 13.6 parts of a reaction mixture having the following composition: 87.4% of m-cresol and 12.6% of mono-tert.-butyl-m-cresol, are withdrawn from the system.

143.3 Parts of m-cresol in a purity of 98.7% (0.1% of diisobutene and 1.2% of isobutene) are collected per hour in collection vessels.

EXAMPLE 7

The experiment described in Example 6 is repeated using p-cresol and mono-tert.-butyl-p-cresol.

12.2 Parts of a reactor mixture which contain 85.5% of p-cresol and 14.5% of mono-tert.-butyl-p-cresol are withdrawn from the system per hour.

The following products are obtained per hour: 77.8 parts of isobutene in a purity of more than 99.9% and 145 parts of p-cresol in a purity of 98.7% (0.1% of diisobutene and 1.2% of isobutene).

What is claimed is:

1. A process for the tertiary dealkylation of a tertiary alkyl containing m- or p-cresol which comprises continuously introducing said tertiary alkyl containing m- or p-cresol and sulfuric acid in an amount of 0.005 weight percent but less than 0.1% by weight sulfuric acid, based upon the weight of the introduced mixture, or an equivalent amount of a sulfonic acid, or a mixture thereof, into a vessel containing 50 to 90 percent by weight of m- or p-cresol or high boiling phenol of boiling point 180°–250° C. withdrawing up to 10 percent of the reaction mixture based upon the feed from the reaction vessel, and maintaining said reaction mixture at a temperature of 180° C. and no greater than 230° C.

2. A Process according to claim 1 wherein the m- or p-cresol is present in an amount of 60 to 70% by weight.

3. A process according to claim 1 wherein a high boiling phenol is employed in an amount of 50 to 90% weight, based upon the weight of the reaction mixture.

4. A process according to claim 1 wherein a portion of the reaction mixture is continuously withdrawn from the reaction vessel.

5. A process according to claim 1 wherein a portion of the reaction mixture is intermittently withdrawn from the reaction vessel.

6. A process according to claim 1 wherein sulfuric acid is employed in the reaction mixture.

7. A process according to claim 1 wherein the amount of reaction mixture withdrawn is 2 to 6% by weight, based upon the weight of the introduced mixture.

8. A process according to claim 1 wherein the amount of reaction mixture withdrawn is in the range of 2 to 6% by weight, based upon the weight of the feed product introduced, 9. A process according to claim 1 wherein the reaction vessel is maintained at a temperature in the range of 180° to 220° C.

10. A process according to claim 9 wherein the reaction vessel is maintained at a temperature of 190° to 210° C.

11. A process according to claim 5 wherein the reaction volume or the reaction vessel is substantially the same as the volume of liquid passing through said vessel, during the reaction, per hour.

12. A process according to claim 1 wherein the reaction occurs at a pressure between 0.5 and 1.5 bars.

13. A process according to claim 6 wherein the sulfuric acid is present in an amount of 0.005 to 0.05% by weight, based upon the weight of the introduced mixture.

14. A process according to claim 13 wherein the sulfuric acid is in the form of a 96 to 98% by weight sulfuric acid, the remainder being water, or oleum or sulfur trioxide.

15. A process according to claim 1 wherein the high concentration of cresol in the reaction mixture is maintained by recycling, into the reaction vessel, a portion of the cresol which issues from the reaction vessel as the reaction product.

16. A process according to claim 1 wherein a gaseous mixture is withdrawn from the reaction vessel and is subjected directly to fractionation in a fractionation unit and the gaseous product issuing from the fractionation unit is subjected to partial condensation and the condensate is recycled as reflux into the fractionation unit and liquid issuing from the fractionation unit is recycled to the reaction vessel.

17. A process according to claim 16 wherein the fractionation is performed at a temperature of 150° to 210° C. at 700-900 mm.Hg. pressure with a reflux ratio of 1.5 to 2.

18. A process according to claim 17 wherein the concentration of cresol in the reaction vessel is controlled by subjecting the gas mixture which issues from the reaction vessel to partial condensation and, during the partial condensation, the ratio of the amount of residual gas flowing out of the condenser to the amount of condensate which flows off, is controlled.

19. A process according to claim 18 wherein cresol is separated off from the residual gas containing cresol and the higher boiling points constituents are recycled into the reaction vessel.

20. A process according to claim 19 wherein the gas mixture which issues from the fractionation unit is subjected to partial condensation only after it has flowed through a second fractionation stage, part of the condensate which flows from the second fractionation being recycled to the first fractionation stage and the remainder being withdrawn as reaction product.

* * * * *

UNITED STATES PATENT AND TRADEMARK OFFICE
CERTIFICATE OF CORRECTION

PATENT NO. : 4,150,243
DATED : April 17, 1979
INVENTOR(S) : BRUCK et al.

It is certified that error appears in the above-identified patent and that said Letters Patent are hereby corrected as shown below:

Column 3, line 3, change "0.5%" to -- 0.05% --.

Signed and Sealed this

Fourth Day of December 1979

[SEAL]

Attest:

SIDNEY A. DIAMOND

Attesting Officer

Commissioner of Patents and Trademarks